United States Patent [19]
Sleigh et al.

[11] Patent Number: 5,998,476
[45] Date of Patent: Dec. 7, 1999

[54] SYNTHETIC POLYUNSATURATED FATTY ACID ANALOGUES

[75] Inventors: Merilyn Joy Sleigh, North Sydney; Fred Widmer, Ryde; Paul Adam Schober, Beacon Hill; Antonio Ferrante, Mount Osmond; Alfred Poulos, Kensington Gardens; Deborah Ann Rathjen, Sheidow Park, all of Australia

[73] Assignee: Peptide Technology Limited, New South Wales, Australia

[21] Appl. No.: 08/836,164

[22] PCT Filed: Oct. 25, 1995

[86] PCT No.: PCT/AU95/00717

§ 371 Date: Jul. 21, 1997

§ 102(e) Date: Jul. 21, 1997

[87] PCT Pub. No.: WO96/13507

PCT Pub. Date: May 9, 1996

[30] Foreign Application Priority Data

Oct. 26, 1994 [AU] Australia ................ PM9065

[51] Int. Cl.⁶ .................................................. A61K 31/20
[52] U.S. Cl. ........................ 514/560; 514/886; 514/895
[58] Field of Search ................................ 514/560, 895, 514/886

[56] References Cited

U.S. PATENT DOCUMENTS

| | | | |
|---|---|---|---|
| 5,604,258 | 2/1997 | Ferrante et al. | 514/560 |
| 5,750,351 | 5/1998 | Medford et al. | 435/7.21 |
| 5,750,572 | 5/1998 | Bruzzese | 514/560 |
| 5,767,156 | 6/1998 | Ferrante et al. | 514/560 |

FOREIGN PATENT DOCUMENTS

| | | |
|---|---|---|
| 0367724A1 | 9/1990 | European Pat. Off. . |
| 0 432 039 A2 | 6/1991 | European Pat. Off. . |
| 0689835 | 1/1996 | European Pat. Off. . |
| 2216418 | 11/1989 | United Kingdom . |
| 2216522 | 11/1989 | United Kingdom . |
| WO/89/07938 | 9/1989 | WIPO . |
| WO/90/08130 | 7/1990 | WIPO . |
| WO/93/00084 | 1/1993 | WIPO . |
| WO/95/09622 | 4/1995 | WIPO . |

OTHER PUBLICATIONS

Patent Abstracts of Japan C–482, p. 154, JP 62–223159 (A).
Patent Abstracts of Japan C–685, p. 71, JP 1–287022 (A).
Patent Abstracts of Japan C–561, p. 141, JP 63–230633 (A) vol. 123 (3) Jul. 17, 1995.
Patent Abstracts of Japan C–717, p. 128, JP 2–53724 (A).

Primary Examiner—Kevin E. Weddington
Attorney, Agent, or Firm—Nixon & Vanderhye

[57] ABSTRACT

The invention provides polyunsaturated fatty acid compounds having antimalarial and/or neutrophil stimulatory activity, or anti-inflammatory activity. The polyunsaturated fatty acids contain a 16–26 carbon chain, 3–6 double bonds and are covalently coupled at the carboxylic acid group to an amino acid. It is preferred that the fatty acid contains 18–22 carbons and that the amino acid is glycine or aspartic acid. Preferred compounds are γ-linolenic acid-glycine, α-linolenic acid-glycine, arachidonic acid-aspartic acid, eicosapentaenoic acid-aspartic acid and docosahexaenoic acid-aspartic acid.

8 Claims, 4 Drawing Sheets

5,998,476

SYNTHETIC POLYUNSATURATED FATTY ACID ANALOGUES

This appln is a 371 of PCT/US95/00717 filed Oct. 25, 1995.

The present invention relates to new polyunsaturated fatty acids having antimalarial activity and/or neutrophil stimulatory activity. In addition, certain of the new polyunsaturated fatty acids depress cytokine activity.

Over half of the world's population is at risk from malaria, with about 500 million acute infections and approximately 1 million deaths recorded each year. (Tropical Diseases Progress in International Research. 1987–1988. Ninth Programme Report. UNDP/World Bank/WHO, Geneva. 43–49; Stevenson M M Preface In: Stevenson M M, Ed. Malaria: Host responses to Infection. CRC Press. Inc). The use of antimalarial drugs is associated with major problems because of increased resistance and toxic side-effects. Most currently used antimalarials are unsuitable for use in children (most at risk of potentially fatal cerebral malaria), pregnant women and the aged.

Neutrophil/macrophage stimulatory agents may have application in the treatment of other infections including Candida sp, Trypanosoma. Schistosomiasis, Tuberculosis, viruses eg herpes, Sindbis viris. Legionella. Listeriosis, Pneumocystsis. Pseudomonas. They would also be useful as adjunct therapy in immunocompromised individuals including those undergoing cancer chemotherapy, transplant recipients and burns patients. In addition, others, so called normal individuals may also be treated, eg. the aged, children under 2, alcoholics, who are known to have poor phagocytic cell activity.

Inflammation may be caused by bacteria, viruses and/or other infective agents, opportunistic infections (which may be consequent on an immunodepressed state, for example resulting from cancer or therapy, particularly cytotoxic drug therapy or radiotherapy), autoimmunity or otherwise. Septic shock is an illustration of a disease involving systemic inflammation. Many of the clinical features of Gram-negative septic shock may be reproduced in animals by the administration of LPS to animals can prompt severe metabolic and physiological changes which can lead to death. Associated with the injection of LPS is the extensive production of pro-inflammatory cytokines such as tumour necrosis factor alpha (TNFα).

Chronic administration of TNF in mice, rats and/or humans causes anorexia, weight loss and depletion of body lipid and protein within 7 to 10 days (Cerami et al, 1985. Immunol. Lett. 11, 173: Fong et al. 1989 J. Exp. Med. 170, 1627. Moldawer et al, Am. J. Physiol, 254 G450–G456. 1988; Fong et al, Am. J Physiol. 256, R659–R665 (1989); McCarthy et al, Am. J. Clin. Nature. 42. 1179–1182). TNF levels have been measured in patients with cancer and chronic disease associated with cachexia.

TNFα has been implicated in the pathology of other diseases associated with chronic inflammation apart form toxic shock and cancer-related cachexia. TNF has been detected in synovial fluid in patients with both rheumatoid and reactive arthritis and in the serum of patients with rheumatoid arthritis (Saxne et al. 1988. Arthrit. Rheumat. 31. 1041). Raised levels of TNF have been detected in renal transplant patients during acute rejection episodes (Maury and Teppo. 1987, J. Exp. Med. 166, 1132). In animals. TNF has been shown to be involved in he pathogenesis of graft-versus-host disease in skin and gut following allogenic marrow transplantation.

Administration of a rabbit anti-murine TNF antibody was shown to prevent the histological changes associated with graft-versus-host disease and to reduce mortality (Piquet et al. 1987, J. Exp. Med. 166, 1220). TNF has also been shown to contribute significantly to the pathology of malaria (Clark et al. 1987, Am. J. Pathol. 129, 192–199). Further, elevated serum levels of TNF have been reported in malaria patients (Scuderi et al. 1986, Lancet 2. 1364–1365).

Elevated pro-inflammatory cytokine levels have further been implicated in causing the pathology and tissue destruction in rheumatoid arthritis, multiple sclerosis (MS) and Crohns disease. Experimentally, anti-bodies which neutralise the activity of cytokine producing cells (eg antibodies against $CD4^+$ T cells or antibodies against CD3) or of the cytokines themselves (eg anti-TNF antibodies) have proved beneficial. High levels of interferon γ are known to be associated with disease exacerbation in MS.

PUFA's have a range of useful biological activities (see for example International Patent Application Nos. WO 93/00084 and WO 95/00607 and the references cited therein). Unfortunately, due to their limited stability in vivo, PUFA's have not achieved widespread use as therapeutic agents. The present inventors have developed a method for coupling amino acids to PUFAs which, while retaining biological activity, have increased stability and solubility. These new polyunsaturated fatty acid (PUFA) compounds have direct antimalarial activity. In addition to their direct antimalarial activity, certain of the novel PUFA activate human neutrophils causing release of granule contents, and exhibit synergy with TNF in the production of superoxide. Activation of human neutrophils by the PUFA results in enhanced ability of these cells to kill malaria parasite (*P. falciparum*) within red blood cells and also the bacteria *Staphylococcus aureus*.

Further, the present inventors have also found that certain of the amino acid coupled PUFA are anti-inflammatory in that they depress the production of pro-inflammatory cytokines while failing to activate neutrophils.

Accordingly, the present invention consists in a polyunsaturated fatty acid compound having antimalarial and/or neutrophil stimulatory activity, or anti-inflammatory activity, the polyunsaturated fatty acid containing a 16–26 carbon chain. 3–6 double bands wherein the polyunsaturated fatty acid is covalently coupled at the carboxylic acid group to an amino acid.

In a preferred embodiment of the present invention the fatty acid contains 18–22 carbons.

In a further preferred embodiment of the present invention the amino acid is glycine or aspartic acid.

In another preferred embodiment of the present invention the fatty acid is an n-3 to n-6 compound.

In yet a further preferred embodiment of the present invention the compound is γ-linolenic acid-glycine, α-linolenic acid-glycine, arachidonic acid-glycine, docosahexaenoic acid-glycine, eicosapentaenoic glycine, γ linolenic acid-aspartic acid, α-linolenic acid-aspartic acid, arachidonic acid-aspartic acid, eicosapentaenoic acid-aspartic acid and docosahexaenoic acid-aspartic acid.

In order that the nature of the present invention may be more clearly understood, a preferred form thereof will now be described with reference to the following examples and figures in which.

Figure 1:
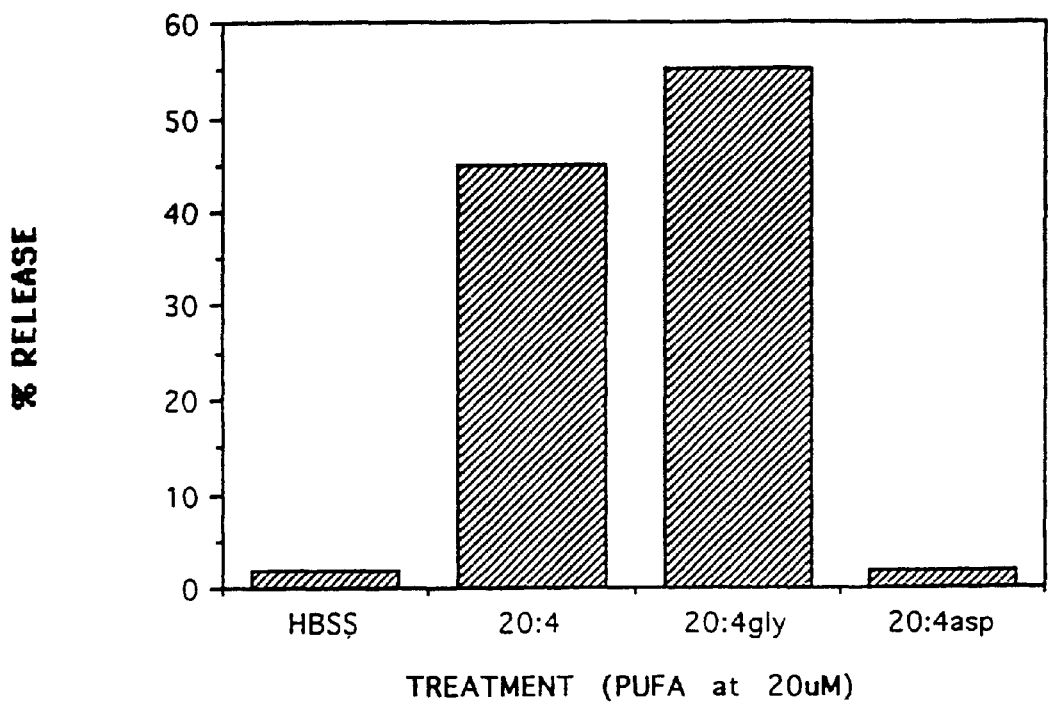
FIGS. 1 and 2 show the effects of PUFAs on release from azurophilic granules.
Figure 2:
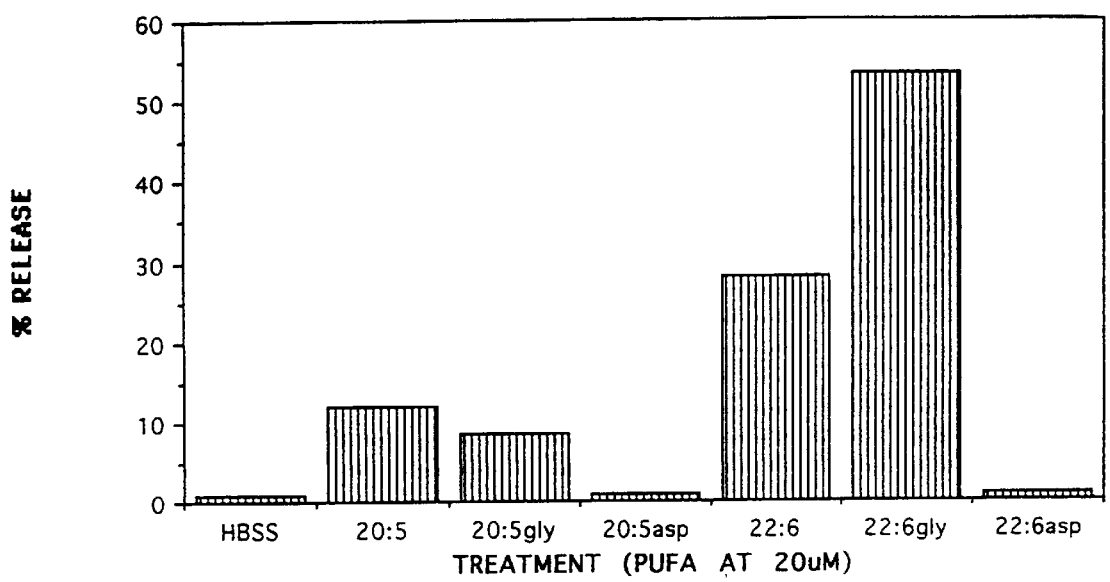
Figure 3:
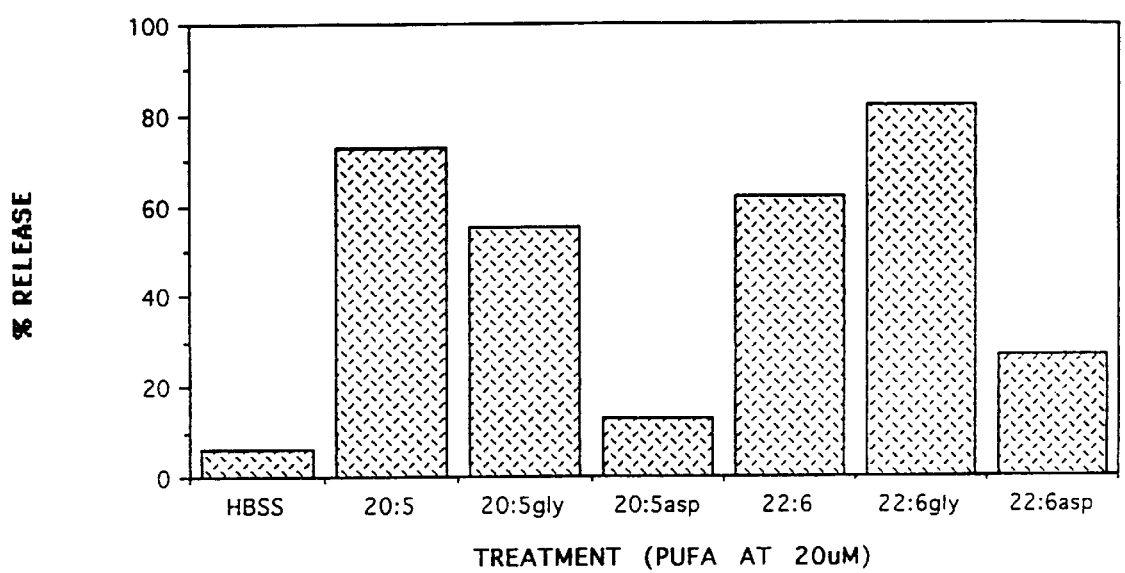
FIG. 3 shows release of neutrophil specific granule contents following treatment with PUFAs.
Figure 4:
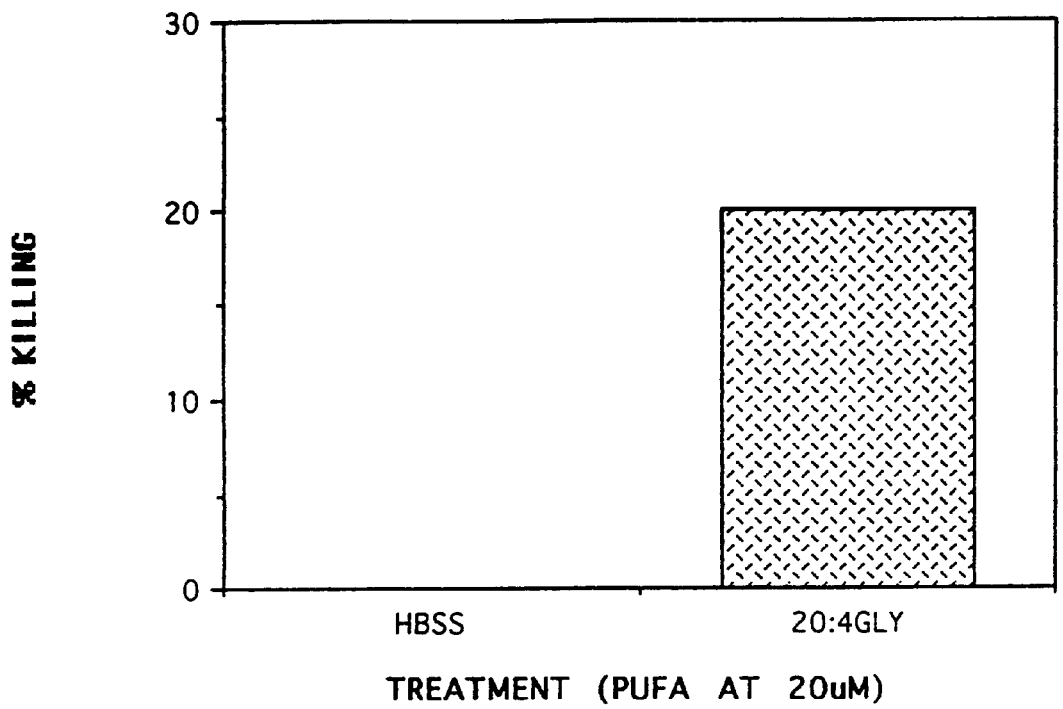
FIG. 4 shows the effect of PUFA on neutrophil mediated killing of *S. aureus*.

In these Figures the following abbreviations are used:

| | |
|---|---|
| 20:4 | Arachidonic acid |
| 20:5 | Eicosapentaenoic acid |
| 22:6 | Docosahexaenoic acid |
| gly | glycine |
| asp | aspartic acid |

Table 1 shows the direct anti-malarial activity of the amino-acid conjugated PUFAs.

Table 2 shows the ability of amino acid conjugated PUFAs to suppress TNFα production and interferon γ production by PHA-stimulated peripheral blood mononuclear cells.

Table 3 shows the ability of amino acid conjugated PUFAs to suppress PHA stimulated proliferation (principally T cell proliferation) of peripheral blood mononuclear cells.

Methods

Preparation of Neutrophils

Heparinised blood from normal healthy individuals was layered onto Ficoll-Hypaque medium of density 1.114 and centrifuged at 600 g for 30–40 min at room temperature. The cells were washed three time in Hanks Balanced Salt Solution (HBSS). Preparation were of 96–99% purity with respect to white blood cells and were >99% viable as judged by their ability to exclude trypan blue. Red blood cell contamination was always less than 1 per neutrophil with platelets being generally absent.

Preparation of Fatty Acid Micelles and Pretreatnent of Neutrophils

To overcome fatty acid insolubility in aqueous solution, mixed dipalmitoyl phosphatidylcholine (DPC, 400 $\mu$g): fatty acid (100 $\mu$g) micelles were prepared in HBSS by sonication. Neutrophils were pretreated for 30 min at 37° C. In some experiments PUFA were solubilized in ethanol.

Measurement of Neutrophil Chemiluminescence

To 100 $\mu$l of neutrophils (1×10$^6$) in HBSS was added 100 $\mu$l of fatty acid micelles or DPC alone and an additional 300 $\mu$l of HBSS. This was followed immediately by the addition of 500 $\mu$l of lucigenin (0.25 mg/ml in PBS) and the resulting light output (mV) measured over time in a luminometer. Experiments were performed in triplicate with cells from a separate individual and values presented represent peak values of the responses.

Measurement of Degranulation

Degranulation was determined by measuring vitamin B12 binding protein (as described by Gottleib et al, 1965, Blood 25: 875–883) and β-glucuronidase release (as described by Kolodeney and Mumford. 1976. Clin. Chem. Acta 70: 247–257).

Bactericidal Assay

Neutrophil bactericidal activity against *Staphylococcus aureus* was measured according to the procedure described by Ferrante and Abell. 1986. Infect. Immun. 51: 607.

Mononuclear Cell Proliferation Assays

Mononuclear cells were separated from peripheral blood of normal human donors as described by Ferrante and Thong (1978 . . . ). The mononuclear cells were resuspended in RPMI-1640 containing 20% human AB serum and placed into 96 well microtrays (50 $\mu$l per well, cell density 4×10$^6$ cells/ml). Fatty acid was then added in 50 $\mu$l and pre-incubated with the cells for 30 min at 37° C. in 5% $CO_2$. Mitogen (PHA, ConA, PWM. *Staph, Aureus*) was then added in 100 $\mu$l and the cells incubated for 66 hours at 37° C. in 5% $CO_2$ before the addition of tritiated thymidine (1 $\mu$Ci/well). After a total of 72 h in culture, the cells were harvested and proliferation (thymidine incorporation) and supernatants assayed for the presence of cytokines.

Cytokine Assays

Cytokine levels in culture supernatants were determined by specific ELISA using anti-cytokine antibodies. The following cytokine levels were determined: TNFα, TNFβ, interferon-γ, IL-1β, IL-2.

Chemical Syntheses

Arachidonic Acid-Glycine-OH

Arachidonic acid (0.50 g) was dissolved in DMF (2.0 mL), HOSu (0.38 g in 0.5 mL DMF) and H-Gly-OtBu.HCl (0.55 g in 1.5 mL DMF) were added. The mixture was cooled in ice bath. DCC (0.41 g in 0.5 mL DMF) was added. N-MM was added and the mixture was stirred for 30 minutes in ice bath and then stirred at room temperature for 20 hours. The reaction did not go to completion and about 20–3-% arachidonic acid was not reacted. More DCC (0.16 g) HOSu (0.19 g). H-Gly-OtBu.HCl (0.20 g) and N-MM (0.24 g) were added and the mixture was stirred for 24 hours. DCU was filtered off and the product was isolated by preparative HPLC and lyophilised to yield a pale green oil (0.67 g. 98%). The oil of arachidonic-Gly-OtBu was redissolved in neat trifluoroacetic acid (40 mL) in ice bath and stirred for 30 min and then at room temperature for further 30 minutes. TFA was evaporated to yield arachidonic-Gly-OH as a muddy green oil (0.53 g). It was purified by HPLC and lyophilised to yield a light yellow gluey solid (0.23 g. 39%).

Purification

Preparative HPLC conditions:

buffer A: 0.1% TFA/$H_2O$, buffer B: 0.1% TFA/10%$H_2O$/90% $CH_3CN$. 40 mL/min, 214 nm. C18 semiPrepPak Stepwise increments of % B: 10–20–30–40–50–60–70–80–90–100% B.

Arachidonic acid eluted at 60% B, arachidonic-Gly-OH eluted at 75–80% B, arachidonic-GlyOtBu eluted at 80–85% B.

1. HPLC buffer: 0.1% TFA/10% $H_2O$/90% $CH_3CN$ 2 mL/min, 214 nm, C18 NovaPak isocratic Retention times of components:

Arachidonic acid: Rt 4.14 min

Arachidonic-Gly-OH: Rt 2.78 min

Arachidonic-Gly-OtBu: Rt 5.23 min

2. $^{13}C$ n.m.r.

Arachidonic-Gly-OH

—(DMISO-d6): 14.1, C20, 22.1, 25.4, 26.4, 26.8, 28.9, 31.0, 34.7, 10×$CH_2$: 40.7, Ga; 127.7, 127.85, 127.93, 128.2, 128.3, 129.6, 130.1, 8×CH; 171.5, C=O, G: 172.5, C1.

3. FAB-MS m/z 362 (M+1)

4. Amino acid analysis

Gly present

Arachidonic-aspartic acid-OH

Arachidonic acid, HOSu and H-Asp(OtBu)-OtBu.HCl were dissolved together in DME (3 mL). The mixture was cooled in ice bath and DCC in DME (0.7 mL) was added. N-MM was added and the mixture was stirred for 20 hours. About 20% arachidonic acid remained. More HOSu (0.19 g), H-Asp(OtBu)-OtBu.HCl (0.30 g). DCC (0.16 g) and N-MM (0.24 g) were added and the mixture was stirred for further 20 hours. DCU was filtered off and the product was isolated by HPLC. The purified Ara-Asp(OtBu)-OtBu was concentrated to an oil and TFA (25 mL) was added. After an hour stirring, TFA was evaporated to yield a dark green oil. Arachidonic-Asp-OH was purified by HPLC. The pure fractions of Ara-Asp-OH were combined, concentrated and lyophilised (in tBu-OH) to yield brown oil (0.38 g, 55%).

Purification

HPLC purification:

buffer A: 0.1% TFA, buffer B: 0.1% TFA+10% $H_2O$+90% $CH_3CN$ 40 mL/min, 214 nm, C18 SemiPrepPak Stepwise increments of % B: 10%–20–30–40–50–60–70–80–85–100% B.

Arachidonic acid eluted at 70% B.

Arachidonic-Asp(OtBu)-OtBu eluted at 80% B.

Arachidonic-Asp-OH eluted at 60% B.

Analysis

1. HPLC buffer: 0.1% TFA+10% $H_2O$+90% $CH_3CN$ 2 mL/min, 214 nm. C18 NovaPak isocratic Retention times:

Arachidonic acid: Rt 4.12 min

Arachidonic-Asp(Otu)-OtBu: Rt 9.52 min

Arachidonic-Asp-OH: Rt 2.31 min

2. $^{13}C$ n.m.r.

Arachidonic-Asp-OH

_(DMSO-d6): 14.1, $CH_3$; 22.1, 25.4, 26.4, 26.8, 28.9, 31.0, 31.5, 34.8. 10×$CH_2$; 34.4, ??; 36.2, Dβ; 48.7, Da; 67.1, ??; 127.7, 127.88, 127.97, 128.18, 128.23, 129.6, 130.1, 8×CH; 171.6, D__; 172.1, C=O, Asp; 172.7, C=O, Arachidonic.

Arachidonic acid

_(DMSO-d6): 14.1, $CH_3$; 22.2, 24.6, 25.4, 26.3, 26.8, 26.9, 28.9, 31.1, 33.3, 10×$CH_2$; 127.7, 127.9, 128.0, 128.2, 128.3, 128.4, 129.3, 130.1, 8×CH; 174.5, C=O.

3. FAB-MS and CI-MS m/z 420 (M+1).

4. Amino acid analysis

Asp present.

Eicosapentaenoic acid-glycine-OH

Eicosapentaenoic acid, H-Gly-OtBu.HCl and HOSu were dissolved together in DMF (4 mL). The mixture was cooled in ice bath and DCC (in 1 mL DMF) was added. N-methylmorpholine was added and the mixture stirred in ice bath for 20 minutes and then at room temperature for 20 hours. 36% of eicosapentaenoic acid remained unreacted. More H-Gly-OtBu.HCl (0.22 g), HOSu (0.15 g), DCC (0.16 g) and N-MM (0.27 g) were added and stirred for further 20 hours. Some eicosapentaenoic acid remained (about 30% by HPLC). The mixture was filtered and the crude product was purified by HPLC to yield Epe-Gly-OtBu as coloured oil (0.49 g, 71%). The oil was redissolved in cold trifluoroacetic acid (30 mL) and stirred for an hour. TFA was evaporated to leave a black oil. The crude Epe-Gly-OH was purified by HPLC to yield 0.13 g (22%) brown oil.

Purification

HPLC purification:

buffer A: 0.1% TFA/$H_2O$ buffer B: 0.1% TFA+10% $H_2O$+90% $CH_3CN$ 40 mL/min. 214 nm. C18 semiPreppak Increments of % B: 10–20–30–40–50–55–60–65–68–70% B.

Epe acid and Epe-Gly-OtBu eluted at 65–70% B. It was able to isolate some pure fractions of Epe-Gly-OH.

Fractions containing the two compounds were combined and repurified.

Under the same conditions as above. Epe-Gly-OH eluted at 60% B.

Analysis

1. Analytical HPLC

Buffer: 0.1% TFA+10% $H_2O$+90% $CH_3CN$ 2 mL/min, 214 nm. C18 Novapak isocratic Retention times of reaction components:

eicosapentaenoic acid: Rt 3.1 min

Epe-Gly-OtBu: Rt 3.9 min

Epe-Gly-OH: Rt 2.1 min

2. $^{13}C$ n.m.r.

(DMSO-d6): 14.3, $CH_3$; 20.2, 25.4, 26.4, 34.8, $CH_2$; 40.7, Ga; 127.2, 127.9, 128.1, 128.2, 128.3, 129.7, 131.8, CH; 171.6, 172.5, C=O.

3. CI-MS m/z 360 (M+1).

Eicosapentaenoic acid-aspartic acid-OH

Eicosapentaenoic acid, H-Asp(OtBu)-OtBu.HCl and HOSu were dissolved together in DMF (4 mL). The mixture was cooled in the ice bath and DCC (in 1 mL DMF) was added. N-Methylmorpholine was added and the mixture was stirred in ice bath for 20 minutes and then at room temperature for 20 hours. About 23% Epe acid by HPLC remained. More H-Asp(OtBu)-OtBu.HCl (0.28 g), HOSu (0.11 g). DCC (0.12 g) and N-MM (0.20 g) were added and the mixture stirred for further 20 hours. About 17% Epe acid remained. The mixture was filtered and the crude Epe-Asp (OtBu)-OtBu was purified by HPLC and yielded 0.83 g (94%) brown oil. Cold trifluoroacetic acid (30 mL) was added to the brown oil and the mixture stirred for an hour. TFA was evaporated to leave a dark brown oil which was redissolved in $CH_3CN$ (10 mL) and was purified by HPLC. The pure Epe-Asp-OH weighed 0.50 g (72%).

Purification

Buffer A: 0.1% TFA/$H_2O$

Buffer B: 0.1% TFA+10% $H_2O$+90% $CH_3CN$ 40 mL/min, 214 nm. C18 semiprepPak

Increments of % B: 10%–20–30–40–50–52–55–57–60–65–68–70% B.

Epe acid eluted at 65% B, Epe-Asp(Ot-Bu)-OtBu eluted at 70% B, Epe-Asp-OH eluted at 55% B.

Analysis

1. Analytical HPLC

Buffer: 0.% TFA+10% $H_2O$+90% $CH_3CN$ 2 mL/min, 214 nm, C18 Novapak, isocratic Retention times:

Epe acid: Rt 3.1 min

Epe-Asp(OtBu)-OtBu: Rt 6.7 min

Epe-Asp-OH: Rt 1.8 min

2. $^{13}C$ n.m.r.

(DMSO-d6): 14.3. $CH_3$; 20.2, 25.3, 25.4, 26.4, 31.5, 34.8, 8×$CH_2$; 36.3, Dβ; 48.7, Da; 127.2, 127.92, 127.97, 128.1, 128.2, 128.3, 129.7, 131.8, 10×CH; 171.9, 172.1, 172.7. 3×C=O.

3. CI-MS m/z 418 (M+1).

Docosahexaenoic acid-glycine-OH

H-Gly-OtBu.HCl and HOSu were dissolved together in DMF (2 ml.) The mixture was cooled in ice bath and docosahexaenoic acid. DCC (in 0.4 mL DMF), and N-methylmorpholine were added. The mixture stirred in ice bath for 30 minutes and then at room temperature for 5 hours. 30% docosahexaenoic acid (Dhe acid) remained. More DCC (0.11 g) was added and the mixture stirred for further 20 hours. About 28% Dhe acid remained. The mixture was filtered and the crude product was purified by HPLC. The lyophilised Dhe-Gly-OtBu (light yellow oil) weighed 0.62 g (92%). Cold TFA (30 mL) was added to the oil and the mixture stirred for an hour. TFA was evaporated to leave a dark brown oil which was redissolved in $CH_3CN$ (10 mL) and was purified by HPLC. The purified Dhe-Gly-OH was lyophilised to leave a dark brown oil (0.27 g. 46%).

Purification

HPLC conditions:

Buffer A: 0.1% $TFA/H_2O$

Buffer B: 0.1% TFA+10% $H_2O$+90% $CH_3CN$ 40 mL/min, 214 nm, C18 semipreppak manual increment of % B: 10%–20–30–40–50–55–60–65–70–73–100% B.

Both Dhe acid and Dhe-Gly-OtBu eluted at 71–73% B. The acid eluted slightly earlier than Dhe-Gly-OtBu.

Dhe-Gly-OH eluted at 60% B.

Analysis

1. Analytical HPLC

Buffer: 0.1% TFA+10% $H_2O$+90% $CH_3CN$ 2 mL/min, 214 nm, C18 NovaPak

Retention times of reaction components:

Dhe acid: Rt 3.6 min

Dhe-Gly-OtBu: Rt 4.5 min

Dhe-Gly-OH: Rt 2.5 min

2. $^{13}C$ n.m.r.

(DMSO-d6): 14.3, $CH_3$; 20.2, 23.2, 25.3, 25.36, 25.42, 35.1, 8×$CH_2$; 40.8, Ga; 127.1, 127.90, 127.98, 128.06, 128.1, 128.27, 128.3, 129.1, 131.8, 6×CH; 171.5, 172.0, 2×C=O.

3. CI-MS m/z 386 (M+1).

Docosahexaenoic Acid-Aspartic Acid-OH

H-Asp(OtBu)-OtBu.HCl and HOSu were dissolved together in DMF (2 mL). The mixture was cooled in ice bath and docosahexaenoic acid. DCC (in 0.4 mL DMF), and N-methylmorpholine were added. The mixture stirred in ice bath for 30 minutes and then at room temperature for 4 hours. 30% docosahexaenoic acid (Dhe acid) remained. More DCC (0.11 g) was added and the mixture stirred for further 20 hours. About 18% Dhe acid remained. The mixture was filtered and the crude product was purified by HPLC. The lyophilised Dhe-Asp(OtBu)-Otu (light yellow oil) weighed 0.73 g (86%). Cold TFA (30 mL) was added to the oil and the mixture stirred for an hour. TFA was evaporated to leave a dark brown oil which was redissolved in $CH_3CN$ (5 mL) and was purified by HPLC. The purified Dhe-Gly-OH was lyophilised to leave a dark brown oil (0.33 g, 49%).

Purification

HPLC conditions:

Buffer A: 0.1% $TFA/H_2O$

Buffer B: 0.1% TFA+10% $H_2O$+90% $CH_3CN$ 40 mL/min, 214 nm. C18 semipreppak manual increment of % B: 10%–20–30–40–50–55–60–65–68–70–73–75% B.

Dhe acid eluted at 73% B. Dhe-Asp(OtBu)-OtBu eluted at 73–75% B. Dhe-Asp-OH eluted at 58% B.

Analysis

1. Analytical HPLC

Buffer: 0.1% TFA+10% $H_2O$+90% $CH_3CN$ 2 mL/min. 214 nm. C18 NovaPak

Retention times of reaction components:

Dhe acid: Rt 3.6 min

Dhe-Asp(OtBu)-OtBu: Rt 8.2 min

Dhe-Asp-OH: Rt 2.0 min

2. $^{13}C$ n.m.r.

(DMSO-d6): 14.3, $CH_3$: 20.2, 23.2, 25.3, 25.4, 25.4, 35.0. 8×$CH_2$: 36.4, Dβ; 48.7, Da; 127.1, 127.9, 127.98, 128.0, 128.1, 128.22, 128.28, 128.3, 129.0, 131.8, CH: 171.6, 171.8, 172.7, 3×C=O.

3. CI-MS m/z 444 (M+1).

Linolenic Acid-Glycine-OH

Linolenic acid, HOSu and H-Gly-OtBu.HCl were dissolved together in DMF (3 mL), the mixture cooled in ice bath and DCC (in 0.3 mL DMF) added. N-MM was added and the mixture stirred for 20 hours, after which time some unreacted linolenic acid remained. More DCC (0.10 g) was added and the mixture stirred for further 20 hours. DCU was filtered off and the product isolated by reversed phase HPLC. The purified product was concentrated to an oil and TFA (30 mL) was added. After an hour stirring, the TFA was evaporated to leave the product as a brown oil which was redissolved in $CH_3CN$ (6 mL) and was purified by HPLC. The pure fractions obtained were combined, concentrated and lyophilised (in t-butanol) to yield a brown oil (0.24 g, 40%).

Purification

HPLC purification:

buffer A: 0.1% $TFA/H_2O$ buffer B: 0.1% TFA+10% $H_2O$+90% $CH_3CN$ 40 mL/min, 214 nm, C18 small prep column Lino-Gly-OH eluted at 65% B, linolenic acid eluted at 67% B, linolenyl-Gly-OtBu eluted also at 67% B but slightly later.

Analysis and Characterisation

1. Analytical HPLC

Buffer A: 0.1% TFA, buffer B: 0.1% TFA/10% $H_2O$/90% $CH_3CN$ 2 mL/min, 214 nm, C18 Novapak 100% B isocratic, retention times of ingredients:

linolenic acid: Rt 3.96 min linolenyl-Gly-OtBu: Rt 4.63 min linolenyl-Gly-OH: Rt 2.59 min 2. $^{13}C$ n.m.r.

(DMSO-d6): 14.2, $CH_3$: 20.2, 25.26, 25.32, 26.8, 28.7, 28.8, 29.2, 35.2, $CH_2$: 40.7, Ga; 127.1, 127.7, 128.1, 130.1, 131.7, CH: 171.6, 172.7, C=O.

3. C.I.-M.S.

m/z 336 (M+1).

Linolenic Acid-Aspartic Acid-OH

Linolenic acid, HOSu and H-Asp(OtBu)-OtBu.HCl were dissolved together in DMF (3 mL), the mixture cooled in ice bath and DCC (in 0.3 mL DMF) added. N-MM was added and the mixture stirred for 20 hours, after which time some unreacted linolenic acid remained. More DCC (0.10 g) was added and the mixture stirred for further 20 hours. DCU was filtered off and the product isolated by reversed phase HPLC. The purified product was concentrated to an oil (0.66 g) and TFA (30 mL) was added. After an hour stirring, the TFA was evaporated to leave the product as a brown oil which was redissolved in $CH_3CN$ (6 mL) and was purified by HPLC. The pure fractions obtained were combined, concentrated and lyophilised (in t-butanol) to yield a brown oil (0.38 g, 54%).

Purification

HPLC purification:

buffer A: 0.1% $TFA/H_2O$ buffer B: 0.1% TFA+10% $H_2O$+90% $CH_3CN$ 40 mL/min, 214 nm. C18 small prep column Lino-Asp-OH eluted at 55% B. linolenic acid eluted at 65% B, linolenyl-Asp(OtBu)-OtBu eluted at 70% B.

Analysis and Characterisation

1. Analytical HPLC

Buffer A: 0.1% TFA, buffer B: 0.1% TFA/10% $H_2O$/90% $CH_3CN$ 2 mL/min, 214 nm, C18 Novapak 100% B isocratic, retention times of ingredients:

linolenic acid: Rt 4.14 min linolenyl-Asp(OtBu)-OtBu: Rt 8.46 min linolenyl-Asp-OH: Rt 2.04 min 2. $^{13}C$ n.m.r.

(DMSO-d6): 14.2, $CH_3$; 20.2, 25.26, 25.34, 26.8, 28.69, 28.72, 28.83, 29.2, 35.2, $CH_2$; 36.3, Dβ; 48.7, Da; 127.1, 127.7, 128.1, 130.1, 131.7, CH; 171.8, 172.2, 172.7, C=O.

3. C.I.-M.S.

m/z 394 (M+1).

Gamma Linolenic Acid-Glycine-OH

γ-Linolenic acid, HOSu and H-Gly-OtBu.HCl were dissolved together in DMF (3 mL), the mixture cooled in ice bath and DCC (in 0.3 mL DMF) added. N-MM was added and the mixture stirred for 20 hours, after which time some unreacted linolenic acid remained. More DCC (0.10 g) was added and the mixture stirred for further 20 hours. DCU was filtered off and the product isolated by reversed phase HPLC. The purified product was concentrated to an oil (0.46 g) and TFA (30 mL) was added. After an hour stirring, the TFA was evaporated to leave the product as a brown oil which was redissolved in $CH_3CN$ (6 mL) and was purified by BPLC. The pure fractions obtained were combined, concentrated and lyophilised (in t-butanol) to yield a brown oil (0.35 g, 58%).

Purification

HPLC purification:

buffer A: 0.1% $TFA/H_2O$ buffer B: 0.1% TFA+10% $H_2O$+90% $CH_3CN$ 40 mL/min, 214 nm, C18 small prep column γ-Lino-Gly-OH eluted at 66% B. γ-linolenic acid eluted at 66% B, γ-linolenyl-Gly-OtBu eluted at 67% B. Compounds eluted in the order listed.

Analysis and Characterisation

1. Analytical HPLC

Buffer A: 0.1% TFA. buffer B: 0.1% TFA/10% $H_2O$/90% $CH_3CN$ 2 mL/min, 214 nm. C18 Novapak 100% B isocratic, retention times of ingredients:

γ-linolenic acid: Rt 4.07 min

γ-linolenyl-Gly-OtBu: Rt 4.85 min

γ-linolenyl-Gly-OH: Rt 2.82 min

2. $^{13}C$ n.m.r.

(DMSO-d6): 14.1, $CH_3$; 22.2, 25.0, 25.4, 26.7, 26.8, 28.8, 28.9, 31.1, 35.1, $CH_2$; 40.7, Ga; 127.7, 127.9, 128.1, 128.2, 129.9, 130.1, CH; 171.6, 172.6, C=O.

3. C.I.-M.S.

m/z 336 (M+1).

Gamma Linolenic-Aspartic Acid-OH

Gamma linolenic acid. HOSu and H-Asp(OtBu)-OtBu.HCl were dissolved together in DMF (3 mL), the mixture cooled in ice bath and DCC (in 0.3 mL DMF) added. N-MM was added and the mixture stirred for 20 hours, after which time some unreacted linolenic acid remained. More DCC (0.10 g) was added and the mixture stirred for further 20 hours. DCU was filtered off and the product isolated by reversed phase HPLC. The purified product was concentrated to an oil (0.65 g) and TFA (30 mL) was added. After an hour stirring, the TFA was evaporated to leave the product as a brown oil which was redissolved in $CH_3CN$ (6 mL) and was purified by HPLC. The pure fractions obtained were combined, concentrated and lyophilised (in t-butanol) to yield a brown oil (0.30 g. 42%).

Purification

HPLC purification:

buffer A: 0.1% $TFA/H_2O$ buffer B: 0.1% TFA+10% $H_2O$+90% $CH_3CN$ 40 mL/min, 214 nm. C18 small prep column Gamma linolenic-Asp-OH eluted at 50% B. linolenic acid eluted at 70% B. linolenyl-Asp(OtBu)-OtBu eluted at 75% B.

Analysis and Characterisation

1. Analytical HPLC

Buffer A: 0.1% TFA, buffer B: 0.1% TFA/10% $H_2O$/90% $CH_3CN$ 2 mL/min, 214 nm, C18 Novapak 100% B isocratic, retention times of ingredients:

gamma linolenic acid: Rt 4.14 min gamma linolenyl-Asp(OtBu)-OtBu: Rt 8.71 min gamma linolenyl-Asp-OH: Rt 2.28 min 2. $^{13}C$ n.m.r.

(DMSO-d6): 14.1, $CH_3$; 22.2, 25.1, 25.4, 26.7, 26.8, 28.7, 28.9, 31.08, 35.1, $CH_2$: 36.3, Dβ: 48.7, Da: 127.8, 127.9, 128.1, 128.2, 130.0, 130.1. CH; 171.9, 172.2, 172.7, C=O.

3. C.I.-M.S.

m/z 394 (M+1).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 1

Inhibition of chloroquine-resistant *P. falciparum* strain K by amino acid conjugated PUFA.

| COMPOUND | % INHIBITION |
| --- | --- |
| Chloroquine | 20.1 |
| Arachidonic acid-glycine-OH | 84.2 |
| Docosahexaenoic acid-glycine-OH | 84.9 |
| Linolenic acid-glycine-OH | 81.5 |

All PUFA at 11μm

TABLE 2

Effect of amino acid conjugated PUFAs on PHA-stimulated TNFa and interferon γ production

| COMPOUND | TNFα | IFNγ |
| --- | --- | --- |
| α-linolenic acid-glycine-OH | 29.3 | 14.5 |
| α-linolenic acid-aspartic acid-OH | 0 | 0 |
| γ-linolenic acid-glycine-OH | 21.5 | 0 |
| γ-linolenic acid-aspartic acid-OH | 4.7 | 0 |
| arachidonic acid-glycine-OH | 26.6 | 35.9 |
| arachidonic acid-aspartic acid-OH | 38.3 | 68.4 |
| eicosapentaenoic acid-glycine-OH | 11 | 68.2 |
| eicosapentaenoic acid-aspartic acid-OH | 17.1 | 66.1 |
| docosahexaenoic acid-glycine-OH | 16.2 | 44 |
| docosahexaenoic acid-aspartic acid-OH | 17.4 | 8.3 |

All PUFA were at 20μM

TABLE 3

Effect of PUFA on cell proliferation induced by PHA

| COMPOUND | % INHIBITION OF PROLIFERATION |
| --- | --- |
| γ-linolenic acid-glycine-OH | 15.6 |
| γ-linolenic acid-aspartic acid-OH | 7.3 |
| α-linolenic acid-glycine-OH | 29 |
| α-linolenic acid-aspartic acid-OH | 15.4 |
| arachidonic acid-glycine-OH | 8 |
| arachidonic acid-aspartic acid-OH | 39.7 |
| eicosapentaenoic acid-glycine-OH | 5.4 |
| eicosapentaenoic acid-aspartic acid-OH | 20.7 |
| docosahexaenoic acid-glycine-OH | 16.6 |
| docosahexaenoic acid-aspartic acid-OH | 21.1 |

All PUFA were at 20μM

We claim:

1. A method of stimulating neutrophil activity and/or treating malarial infection and/or inflammation in a subject requiring such treatment, the method comprising administering to the subject a polyunsaturated fatty acid containing a 16–26 carbon chain, 3–6 double bonds wherein the polyunsaturated fatty acid is covalently coupled at the carboxylic acid group to an amino acid selected from glycine and aspartic acid.

2. A method as claimed in claim 1 in which the fatty acid contains 18–22 carbons.

3. A method as claimed in claim 1 in which the fatty acid is an n-3 to n-6 compound.

4. A method as claimed in claim 1 in which the fatty acid is γ-linolenic acid.

5. A method as claimed in claim 1 in which the fatty acid is α-linolenic acid.

6. A method as claimed in claim 1 in which the fatty acid is arachidonic acid.

7. A method as claimed in claim 1 in which the fatty acid is eicosapentaenoic acid.

8. A method as claimed in claim 1 in which the fatty acid is docosahexaenoic acid.

* * * * *